(12) United States Patent
Cerda et al.

(10) Patent No.: US 8,247,236 B2
(45) Date of Patent: *Aug. 21, 2012

(54) DETECTING LEUCINE AND ITS ISOMERS USING DIFFERENTIAL ESTERIFICATION MASS SPECTROMETRY

(75) Inventors: Blas Cerda, Milford, MA (US); Alex Cherkasskiy, West Roxbury, MA (US); Yijun Li, Worcester, MA (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/084,250

(22) Filed: Apr. 11, 2011

(65) Prior Publication Data

US 2011/0189780 A1    Aug. 4, 2011

Related U.S. Application Data

(63) Continuation of application No. 11/744,518, filed on May 4, 2007, now Pat. No. 7,923,257.

(51) Int. Cl.
*G01N 33/00* (2006.01)
*G01N 33/50* (2006.01)

(52) U.S. Cl. .......................... 436/90; 436/173
(58) Field of Classification Search .......... 436/90
See application file for complete search history.

(56) References Cited

U.S. PATENT DOCUMENTS

| | | | | |
|---|---|---|---|---|
| 6,800,489 | B2 * | 10/2004 | Dooley | 436/173 |
| 2006/0009922 | A1 | 1/2006 | Chace | |
| 2006/0014297 | A1 | 1/2006 | Chace | |
| 2006/0234326 | A1 | 10/2006 | Cerda | |

FOREIGN PATENT DOCUMENTS

WO    WO-2005/021779    * 3/2005

OTHER PUBLICATIONS

Seymour, J. L. et al. "Distinction and quantitation of leucine-isoleucine isomers and lysine-glutamine isobars by electrospray ionization tandem mass spectrometry (MSn, n=2, 3) of copper(II)-diimine complexes," Journal of Mass Spectrometry 35, 566-571 (2000).*

Campana Filho et al. "Kinetics and yield of the eserification of amino acids with thionyl chloride in n-propano," J. Chromatogr., 1982, 236, 197-200.

(Continued)

*Primary Examiner* — Yelena G Gakh
*Assistant Examiner* — Michelle Adams
(74) *Attorney, Agent, or Firm* — Fish & Richardson P.C.

(57) ABSTRACT

Methods of evaluating molecular isomers of branched-chain amino acids are featured. The methods can include: derivatizing one or more molecular isomers of branched-chain amino acids in a sample comprising a branched-chain amino acid labeled with one or more heavy atoms as a first standard; adding, to the sample, after derivatization, a nonderivatized or derivatized branched chain amino acid that is labeled with one or more heavy atoms, as a second standard; evaluating the sample using tandem mass spectrometry; and detecting peaks indicative of derivatized and nonderivatized forms of one or more branched-chain amino acids in the sample.

26 Claims, 5 Drawing Sheets

OTHER PUBLICATIONS

Chuang and Shin, "Maple syrup urine disease (branched-chain ketoaciduria)," The Metabolic and Molecular Bases of Inherited Disease, 2001, 8th ed., Scriver et al. (eds.), McGraw-Hill, New York, NY, p. 1971.

Chuang et al., "Structural and Biochemical Basis for Novel Mutations in Homozygous Israeli Maple Syrup Urine Disease Patients," J. Biol. Chem., 2004, 279:17792-17800.

Hasegawa et al., "Assessment of the metabolic chiral inversion of D-leucine in rat by gas chromatography-mass spectrometry combined with a stable isotope dilution analysis," Drug Metabolism and Disposition, 28:920-24 (2000).

Higashi et al., "Liquid chromatography-mass spectrometric assay of androstenediol in prostatic tissue: Influence of androgen deprivation therapy on its level," Steroids, 2006, 71:1007-1013.

Indo and Matsuda, "Molecular defects of the branched-chain-ketoacid dehydrogenase complex: maple syrup urine disease due to mutation of the E1 or E1β subunit gene," Alpha-Keto Acid Dehydrogenase Complexes, 1996, pp. 227-247.

Matthews et al., "Alloisoleucine Formation in Maple Syrup Urine Disease: Isotopic Evidence for the Mechanism," Pediatr. Res., 1980, 14:854-857.

Morris et al., "Clinical and Biochemical Observations on an Apparently Nonfatal Variant of Branched-Chain Ketoaciduria (Maple Syrup Urine Disease)," Pediatrics, 1961, 28:918-923.

Oglesbee et al, "Second-tier test for quantification of allosoleucine and branched-chan amino acids in dried blood spots to improve newborn screening for maple syrup urine disease (MSUD)," Clin. Chem., 54:542-49 (2008).

Schadewaldt et al., "Significance of L-Alloisoleucine in Plasma for Diagnosis of Maple Syrup Urine Disease," Clin. Chem., 1999, 45(10):1734-1740.

Schadewaldt et al., "Whole-Body L-Leucine Oxidation in Patients with Variant Form of Maple Syrup Urine Disease," Pediat. Res., 2001, 49:627-635.

Schulman et al., "A New Variant of Maple Syrup Urine Disease (Branched Chain Ketoaciduria)," Am. J. Med., 1970, 49:118-124.

Snyderman et al., "Maple Syrup Urine Disease, With Particular Reference to Dietotherapy," Pediatrics, 1964, 34:454-472.

Supplementary European Search Report in EP08747663 dated Jul. 26, 2010.

Wendel et al., "Interralation between the metabolism of L-isoleucine and L-allo-isoleucine in patients with maple syrup urine disease," Pediatr. Res., 1989, 1:11-14.

Westall et al., "Maple syrup urine disease," Am. J. Dis. Child., 1957, 94:571-572.

Zoppa et al., "Method for the quantification of underivatized amino acids on dry blood spots from newborn screening by HPLC-ESI-MS/MS," J. Chrom. B., 831:267-73 (2006).

Non-Final Office Action issued in U.S. Appl. No. 11/744,518, mailed Oct. 29, 2009.

Fish & Richardson, PC. Response to Office Action issued in U.S. Appl. No. 11/744,518, mailed Feb. 25, 2010.

Final Office Action issued in U.S. Appl. No. 11/744,518, mailed Apr. 16, 2010.

Fish & Richardson, P.C., Response to Final Office Action issued in U.S. Appl. No. 11/744,518, mailed Jul. 16, 2010.

Advisory Action issued in U.S. Appl. No. 11/744,518, mailed Jul. 28, 1010.

Fish & Richardson, P.C., Request for Continued Examination and Amendment in U.S. Appl. No. 11/744,518, mailed on Oct. 18, 2010.

Notice o f Allowance and Issue Fee issued in U.S. Appl. No. 11/744,518, mailed Dec. 6, 2010.

Fish & Richardson, P.C., Amendment after Notice of Allowance in U.S. Appl. No. 11/744,518, mailed Jan. 14, 2011.

Chace et al., "Rapid diagnosis of maple syrup urine disease in blood spots from newborns by tandem mass spectrometry," Clin. Chem., 41:62-68 (1995).

Chace et al., "Use of tandem mass spectrometry for multianalyte screening of dried blood specimens from newborns," Clin. Chem., 49:1797-1817 (2003).

European Examination Report; Application No. 08747663.6; mailed Apr. 6, 2011; pp. 1-4.

European Examination Report; Application No. 08747663.6; mailed Aug. 31, 2011; ; pp. 1-4.

European Search Report; Application No. 08747663.6; mailed Aug. 6, 2010; pp. 1-8.

International Search Report and Written Opinion; Application No. PCT/US08/62685; mailed Aug. 7, 2008; pp. 1-11.

Ogier de Baulny & Saudubray, "Branched-Chain Organic Acidurias," *Seminars in Neonatology* 7:65-74, 2002.

Chinese Office Action; Application No. 200880022888.1; issuing date: May 11, 2012; Applicant: PerkinElmer Health Sciences, Inc.; 5 pages.

* cited by examiner

DETECTING LEUCINE AND ITS ISOMERS USING DIFFERENTIAL ESTERIFICATION MASS SPECTROMETRY

CROSS-REFERENCE TO RELATED APPLICATIONS

This application claims the benefit of priority of U.S. patent application Ser. No. 11/744,518, filed on May 4, 2007, now U.S. Pat. No. 7,923,257. This prior application is incorporated herein by reference in its entirety.

BACKGROUND

Mass spectrometry is a technique used to analyze the mass-to-charge ratio of ions. It can be used to provide composition of a particular analyte by generating a mass spectrum representing components of the analyte (tandem mass spectrometry). Some of its applications include screening biological samples for markers of specific disorders or diseases.

SUMMARY

Mass spectrometry (MS) can be used to evaluate branched-chain amino acids, and can be used to distinguish between branched-chain amino acids that are molecular isomers, e.g., leucine, isoleucine, and allo-isoleucine. Methods for detecting isomeric branched-chain amino acids can include derivatizing a sample, e.g., esterifying the sample. However, such amino acids typically are derivatized with different efficiencies.

Different derivatization efficiencies can be utilized to improve specificity and/or sensitivity of detection of various branched-chain amino acids. Internal standards, e.g., branched-chain amino acids labeled with one or more heavy isotopes, can be used to track derivatization efficiency and thereby enhance detection and quantification of branched-chain amino acids in a sample. In some cases, at least two internal standards are used. The standards are isomeric with the branched chain amino acids, but have different molecular weight from one another by virtue of having different heavy isotope labeling. In some implementations, one standard is added prior to derivatization, and the other is added subsequent to derivatization. In some implementations, one standard corresponds to a derivatized amino acid and the other corresponds to a nonderivatized amino acid.

In one aspect, a method of evaluating molecular isomers of branched-chain amino acids, e.g., leucine, isoleucine, and allo-isoleucine, is featured. The method includes derivatizing one or more molecular isomers of branched-chain amino acids in a sample comprising a branched-chain amino acid labeled with one or more heavy atoms as a first standard. The first standard can be, e.g., leucine, isoleucine, and allo-isoleucine. After derivatization, a nonderivatized or a derivatized branched-chain amino acid that is labeled with one or more heavy atoms is added to the sample as a second standard. The second standard can be, e.g., leucine, isoleucine, and allo-isoleucine. The sample is evaluated using tandem mass spectrometry, and peaks indicative of derivatized and nonderivatized forms, e.g., butylated and unbutylated forms, of one or more branched-chain amino acids, e.g., leucine, isoleucine, and allo-isoleucine, in the sample are detected.

The derivatized forms of the first and second standard can have different molecular weights as a result of different heavy atom labeling. The non-derivatized forms of the first and second standard can have different molecular weights as a result of different heavy atom labeling.

The method can further include determining the derivatization efficiency of a branched-chain amino acid by reference to the first and second standards. The method can further include determining the concentration of a branched chain amino acid in the sample using the derivatization efficiency.

The derivatizing can be esterification, e.g., carried out with an alcohol, e.g., butanol, isopropanol, ethanol, and methanol. The esterification step can include adjusting one or more parameters, e.g., temperature and incubation time, to decrease the level of esterification of one or both of isoleucine and allo-isoleucine. Less than 100% of branched-chain amino acids can be derivatized, e.g., esterified, e.g., about 80-94% of leucine can be esterified, about 5-20% of isoleucine can be esterified, and about 25-40% of allo-isoleucine can be esterified.

The sample can further include a third and/or fourth standard prior to derivatization. The third and/or fourth standard can be, e.g., leucine, isoleucine, and allo-isoleucine. The derivatized forms of the first, second, third, and (optionally) fourth standards can have different molecular weights as a result of different heavy atom labeling. The non-derivatized forms of the first, second, third, and (optionally) fourth standards can have different molecular weights as a result of different heavy atom labeling. The method can include other features described herein.

In another aspect, a method of diagnosing a metabolic disorder is featured. The method includes treating a sample, e.g., a sample including blood, from a subject, under conditions in which branched-chain amino acids, e.g., leucine, isoleucine, and allo-isoleucine, in the sample are derivatized. The subject can be a human, e.g., a newborn human. The sample includes a branched-chain amino acid, e.g., leucine, isoleucine, and allo-isoleucine, labeled with one or more heavy atoms as a first standard. After derivatization, a non-derivatized or derivatized branched-chain amino acid, e.g., leucine, isoleucine, and allo-isoleucine, that is labeled with one or more heavy atoms is added as a second standard. The sample is evaluated using tandem mass spectrometry and peaks indicative of derivatized and nonderivatized forms, e.g., butylated and unbutylated forms, of one or more branched-chain amino acids (e.g., leucine, isoleucine, and allo-isoleucine) in the sample are detected. An altered level of one or more branched-chain amino acids in the sample relative to the level in one or more reference samples is an indication that the subject has, or is at risk of developing, a metabolic disorder characterized by altered levels of one or both of branched-chain amino acids and branched-chain ketoacids.

The metabolic disorder can be, e.g., Maple Syrup Urine Disorder (MSUD), e.g., a classic MSUD, an intermediate MSUD, an intermittent MSUD, a thiamine-responsive MSUD, and/or an E3-deficient MSUD. The disorder can be further characterized by one or more of the following: ketoacidosis, neurological abnormality, and developmental disturbance.

The method can further include determining the derivatization efficiency of a branched-chain amino acid by reference to the first and second standards. The method can further include determining the concentration of a branched chain amino acid in the sample using the derivatization efficiency.

The derivatizing can be esterification, e.g., carried out with an alcohol, e.g., butanol, isopropanol, ethanol, and methanol. The esterification step can include adjusting one or more parameters, e.g., temperature and incubation time, to decrease the level of esterification of one or both of isoleucine and allo-isoleucine. Less than 100% of branched-chain amino acids can be derivatized, e.g., esterified, e.g., about 80-94% of leucine can be esterified, about 5-20% of isoleucine can be esterified, and about 25-40% of allo-isoleucine can be esterified.

The derivatized forms of the first and second standard can have different molecular weights as a result of different heavy atom labeling. The non-derivatized forms of the first and second standard can have different molecular weights as a result of different heavy atom labeling.

The sample can further include a third and/or fourth standard prior to derivatization. The third and/or fourth standard can be, e.g., leucine, isoleucine, or allo-isoleucine. The derivatized forms of the first, second, third, and (optionally) fourth standards can have different molecular weights as a result of different heavy atom labeling. The non-derivatized forms of the first, second, third, and (optionally) fourth standards can have different molecular weights as a result of different heavy atom labeling. The method can include other features described herein.

In another aspect, the disclosure features a method of obtaining a metabolic profile of a subject, e.g., a human. The method includes providing a biological sample from a subject. The sample includes one or more molecular isomers of branched-chain amino acids, e.g., leucine, isoleucine, and allo-isoleucine, and a branched-chain amino acid, e.g., leucine, isoleucine, and allo-isoleucine, labeled with one or more heavy atoms as a first standard. One or more of the branched-chain amino acids in the sample are derivatized. After derivatization, a nonderivatized or derivatized branched-chain amino acid, e.g., leucine, isoleucine, and allo-isoleucine, that is labeled with one or more heavy atoms is added to the sample as a second standard. The sample is evaluated using tandem mass spectrometry. Peaks indicative of derivatized and nonderivatized forms, e.g., butylated and unbutylated forms, of one or more branched-chain amino acids in the sample are detected. The presence of the branched-chain amino acids in the sample is used to obtain the metabolic profile of the subject. The metabolic profile can include information about other molecules. The method can include other features described herein.

In one aspect, this disclosure features a method of evaluating molecular isomers of small molecules, e.g., metabolites, e.g. branched-chain amino acids. The molecular isomers are derivatized before being evaluating using tandem mass spectrometry. A first standard is added to the sample before derivatization; a second standard is added after derivatization. The second standard can be derivatized or not derivatized. The first and second standards have different molecular weights after derivatization, e.g., so that their peaks are distinguishable by mass spectrometry. For example, they have different heavy isotopic labeling so that their peaks are shifted from one another and from isomers in the sample. The method can include other features described herein.

In one aspect, this disclosure features a method of evaluating molecular isomers of branched-chain amino acids, e.g., leucine, isoleucine, and allo-isoleucine. The method includes: derivatizing one or more molecular isomers of branched-chain amino acids in a sample; adding, to the sample, a nonderivatized or derivatized branched chain amino acid that is labeled with a heavy atom, as a standard; evaluating the sample using tandem mass spectrometry; and detecting peaks indicative of derivatized and nonderivatized forms of one or more branched-chain amino acids in the sample. The method can include other features described herein.

In another aspect, a method of evaluating molecular isomers of branched-chain amino acids is featured. The method includes: derivatizing one or more molecular isomers of branched-chain amino acids in the sample; evaluating the sample using tandem mass spectrometry; detecting peaks indicative of derivatized and nonderivatized forms of one or more branched-chain amino acids in the sample; and determining the concentration of branched-chain amino acids in the sample using information about the derivatization efficiency for each of the different isomers. The method can include other features described herein.

Another aspect features a composition that includes: a first standard including nonderivatized or derivatized branched-chain amino acid labeled with one or more heavy atoms; and a second standard including derivatized branched-chain amino acid labeled with one or more heavy atoms. The first and second standards are isomeric, but have different molecular weights due to different heavy atom labeling. The branched-chain amino acid can be, e.g., leucine, isoleucine, and allo-isoleucine. The composition can further include an experimental sample comprising branched-chain amino acids that are isomers. The composition can include other features described herein.

A kit for evaluating isomers of branched-chain amino acids, e.g., leucine, isoleucine, and allo-isoleucine, is also featured. The kit includes: a first standard of non-derivatized branched-chain amino acid labeled with one or more heavy atoms; and a second standard of nonderivatized or derivatized branched-chain amino acid labeled with one or more heavy atoms. The nonderivatized forms of the first and second standard have different molecular weights as a result of different heavy atom labeling. The kit can include other features described herein, e.g., the kit can further include computer software useful for detecting branched-chain amino acids.

In some embodiments, the methods herein are used to analyze a sample that has not been processed by another separation method, i.e., it has not been processed by chromatography.

The methods described herein can be used to implement cost efficient and rapid diagnostic assays.

All patents, patent applications, and references cited herein are hereby incorporated by reference.

DETAILED DESCRIPTION

It is frequently important to distinguish between or among different molecular isomers. The methods described herein can be used to detect one or more molecular isoforms, e.g., of branched-chain amino acids, e.g., leucine, isoleucine, and allo-iso leucine, in a manner that uniquely identifies each isomer with the use of a tandem mass spectrometer. The inclusion of one or more standards in a sample can be used to determine the concentration of a particular isomer in a sample. In addition, inclusion of one or more standards can be used to determine differential derivatization efficiencies of various iso forms. In some implementations, derivatization efficiencies can be determined for various isoforms prior to analysis of a desired sample. The methods described herein are applicable to other isomers that have differential derivatization properties.

In some implementations, samples are evaluated to detect both derivatized and nonderivatized forms of molecular isomers (e.g., by acquiring data on MS with scans appropriate for derivatized and nonderivatized forms). Then, information about the derivatization rate of the isomers (obtained during the same evaluation process or in a separate analysis) can be used to infer the original concentration of each isomer. This is particularly important in cases where, for example, the non-derivatized forms cannot be separately detected, for example, where they produce the same peaks in tandem mass spectrometry (MS). Information about derivatization rates can be determined by using standards, e.g., an internal standard for one or more of the derivatized and/or nonderivatized isomers. The internal standard can be labeled with one or more heavy isotopes so its peaks are shifted from those of the isomers in a sample (e.g., from a natural source). Alternatively, external standards or parallel samples containing such standards can be used to determine derivatization rate (see, e.g., Table 1 in Example 2).

Figure 2:
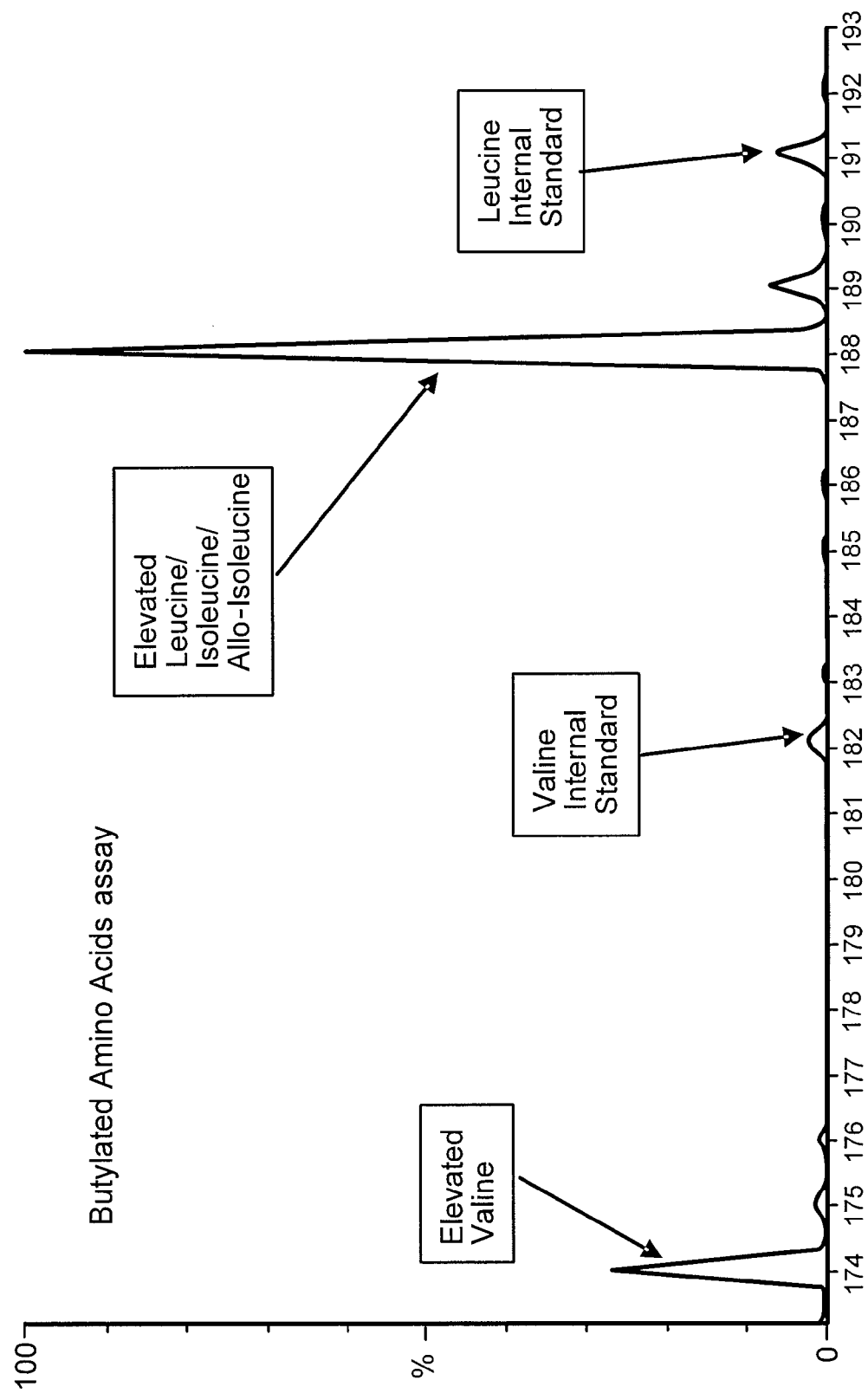
FIG. 2 is a graph depicting an example of measurement of elevated levels of valine and leucine/isoleucine/allo-isoleucine in a dried blood spot.

In one implementation, two internal standards are used to evaluate the concentration of leucine (Leu), isoleucine (Ile), and/or allo-isoleucine (allo-Ile) in a sample. Leu, Ile and allo-Ile are all structural isomers and thus when they are butyl esters all appear at the same m/z (+188) in the MS/MS experiment (see, e.g., FIG. 2). For example, to evaluate these isomers in a sample, the sample is derivatized with an alcohol (e.g., butanol) in acid (e.g., 3N HCl) to generate n-butyl esters of the analytes of interest. The sample can include a first standard with a derivatized form of an isomer (or with a nonderivatized form that is derivatized upon processing of the sample). Using alcohols of different alkyl chain lengths (e.g., ethanol, methanol, butanol, isopropanol) may improve the specificity of the separation. For example, the discrimination of Ile during esterification may be even more pronounced when isopropanol is used as the derivatizing reagent.

The derivatized sample is reconstituted in a solvent amenable for tandem mass spectrometry (MS/MS) analysis and a second standard (e.g., a nonderivatized internal control, or a derivatized internal control) for one of the isomers (e.g., for Ile or allo-Ile) can be added. Peaks detected by tandem MS (e.g., using scans appropriate for derivatized and nonderivatized forms) can then be analyzed. The combination of the internal controls (e.g., first derivatized standard and second nonderivatized standard) can be used to identify and quantitate the concentration of unbutylated and butylated forms.

The combination of the internal standards can also be used, e.g., to provide information about the relative derivatization rates, from which one can compute the actual concentration of an isomer in the original sample. Alternatively, information disclosed herein can be used as the relative derivatization rates.

In some embodiments, the sample includes Leu internal standard in butylated form and Ile internal standard in non-butylated form. In one implementation, at least one (either Leucine, Isoleucine and/or Allo-Isoleucine) of internal standards is esterified using an alcohol (as part of the assay or as part of the assay component (i.e., pre-esterified internal standard)) and at least one of the internal standards (Leucine, Isoleucine or Allo-Isoleucine) is added to the assay reaction mixture in non-esterified form after the esterification step. The internal standards for Leu, Ile and allo-Ile may or may not have same isotopic labels. The isotopic label can be any of the stable isotopes potentially allowing for differentiation between or among species with the same molecular weight via MS/MS acquisition.

The methods and compositions described herein can include the use of various combinations of internal standards. For example, they can include one, two or three internal standards (each including one of Leu, Ile, or allo-Ile) that are nonderivatized and become derivatized upon processing of the sample. Another internal standard can be added after derivatization. The added standard can be a nonderivatized Leu, Ile, or allo-Ile or a derivatized Leu, Ile, or allo-Ile. The combination of the standards can be used to calculate derivatization efficiencies and/or concentrations of isomers in a particular sample (see, e.g., Example 3).

The methods described herein can be used widely, for example, in any application that requires the separate measurement of Leu and Ile/allo-Ile. For example, these techniques can be used to quantitate the yields of an organic chemistry reaction, (including industrial or other commercial scale synthetic reactions). By measuring a mixture of Leu and Ile with a non-derivatized assay one can obtain the full complement of the combined concentrations (Leu+Ile). Measuring the mixture after butylation one will obtain mainly the concentration of Leu in the mixture. Therefore, subtracting the concentration obtained with the derivatized assay from that obtained from the nonderivatized assay the concentration of Ile will be obtained.

Exemplary Applications

The methods described herein have a variety of applications, including, inter alia, screening for various metabolic disorders, e.g., maple syrup urine disorder (MSUD), quantitating the yields of organic reactions, obtaining metabolic profiles, and identifying compounds that modulate levels of branched-chain amino acids that are isomers.

Maple Syrup Urine Disorder

Maple Syrup Urine Disorder (MSUD) is an inborn error of metabolism that can be screened using tandem mass spectrometry (MS/MS).

MSUD is caused by a deficiency in the branched-chain α-ketoacid dehydrogenase (BCKDH) complex. Accumulations of branched-chain amino acids (BCAAs) and branched-chain α-ketoacids (BCKAs) in patients with MSUD induce ketoacidosis, neurological disorders, and developmental disturbance. BCAAs' and BCKAs' influence on the nervous system can cause clinical problems derived from impaired function of the central nervous system. Damage to neuronal cells found in MSUD patients occurs presumably because of higher concentrations of both blood BCAAs or BCKAs (Indo and Matsuda, Patel, M. S. Roche, T. E. Harris, R. A. eds. *Alpha-Keto Acid Dehydrogenase Complexes* 1996:227-247

Figure 1:
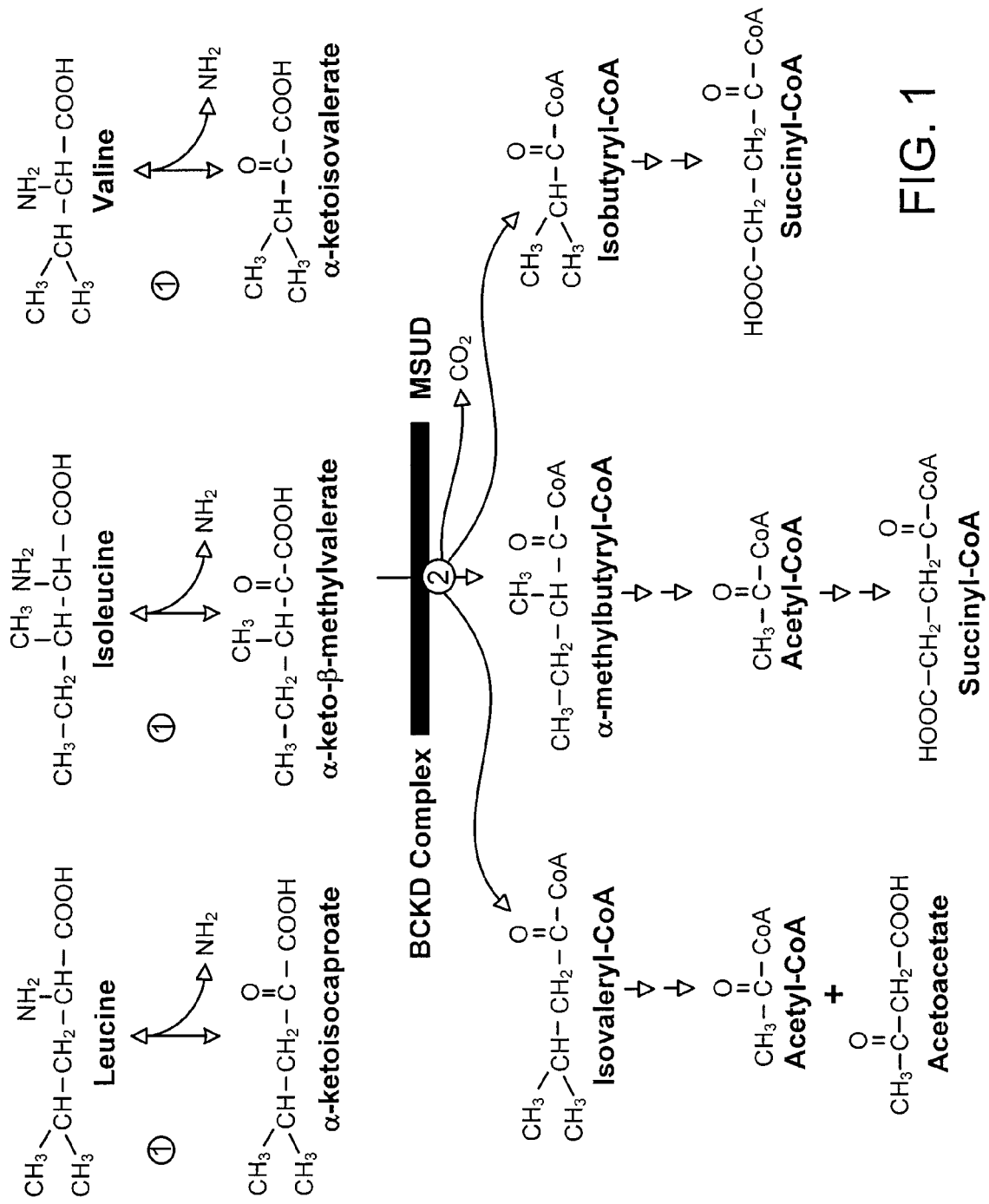
FIG. 1 is a schematic overview of oxidative degradation of branched-chain amino acids (BCAA) leucine, isoleucine, and valine. The transamination of BCAA is catalyzed by a single branched-chain aminotransferase (reaction 1) that exists as both the cytosolic and mitochondrial iso forms. The oxidative decarboxylation of branched-chain ketoacids is catalyzed by the single mitochondrial branched-chain-ketoacid dehydrogenase complex (reaction 2). The metabolic block at the second reaction results in Maple Syrup Urine Disorder.

Bilkhauser Basel, Switzerland, 1996; Chuang and Shih, Scriver, C. R. Beaudet, A. L. Sly, W. S. Valle, D. eds. *The Metabolic and Molecular Bases of Inherited Disease* 8th ed. 2001:1971-2005 McGraw-Hill New York, N.Y., 2001; Westall et al., *Am. J. Dis. Child.* 94:571-572, 1957). The metabolic pathway causing MSUD is depicted in FIG. 1 (Chuang and Shih).

MSUD is classified into several forms. Among these forms, the classic form has the earliest onset and is the most severe (Chuang and Shih). The five forms of MSUD are as follows.

1. Classic MSUD. In classic MSUD, the most common form of the disorder, activity of the BCKDH complex is <2% of normal subjects, and 50% or more of the keto acids are derived from leucine. Affected newborns appear normal at birth, with symptoms developing between 4 and 7 days of age. The infants show lethargy, weight loss, metabolic derangement, and progressive neurologic signs of altering hypotonia and hypertonia, reflecting severe encephalopathy. Odor of the urine resembles maple syrup. Seizures and coma usually occur, followed by death if untreated. Early treatment significantly improves the intellectual outcome but poor biochemical control may adversely affect performance. Blood levels of leucine increase before presentation of symptoms (Chuang and Shih).

Two other forms, usually with milder symptoms that appear after the neonatal period, are intermediate and intermittent MSUD.

2. Intermediate MSUD. Patients with this form have no severe ketoacidosis attack but fail to thrive, and have mild systemic acidosis and developmental delay. The levels of plasma BCAAs and BCKAs are persistently increased. Protein restriction is an effective treatment but thiamine administration is not. These patients have 3 to 30% residual BCKDH activity (Schulman et al., *Am. J. Med.* 49: 118-124, 1970; Schadewaldt et al., *Pediat. Res.* 49: 627-635, 2001).

3. Intermittent MSUD. Patients with this form have recurrent episodic ataxia, lethargy, semicoma, and occasional elevated plasma BCAAs and BCKAs after infections or other acute illnesses. They usually have normal intellect, although in some cases with repeated ketoacidosis attacks, intellect is borderline or less. Dietary protein restriction is an effective treatment. The levels of BCKDH activity are higher than in the classic form of the disease (Morris et al., *Pediatrics* 28: 918-923, 1961).

4. Thiamine-responsive MSUD. Patients with this form have hyperaminoacidemia similar to the intermediate form, but can be successfully treated with thiamine administration. The BCKDH complex activity in the thiamine-responsive MSUD patient is 2 to 40% of normal subjects. Further studies showed that the primary defect in thiamine-responsive MSUD is reduced affinity of the mutant BCKDH for TPP because of a mutation in the E2 protein (Chuang et al., *J. Biol. Chem.* 279:17792-17800, 2004).

5. E3-Deficient MSUD. E3-deficient MSUD, or MSUD type III, presents a combined deficiency of BCKDH, pyruvate dehydrogenase, and -ketoglutarate dehydrogenase complexes. This is the result of E3 being a common component of all 3 mitochondrial multienzyme complexes. Patients with this form show failure to thrive, hypotonia, lactic acidosis, and developmental delay. Lactate, pyruvate, and -ketoglutarate are elevated as well as BCAAs and BCKAs. The prognosis of this form varies with levels of residual enzymatic activity. Neuropathological studies showed Leigh encephalopathy. In some cases, treatments with biotin, lipoic acid, and dichloroacetate are effective (Chuang and Shih).

The biochemical markers for MSUD are L-Leucine (Leu), L-Valine (Val), L-Isoleucine (Ile) and L-Allo-Isoleucine (allo-Ile). The presence of L-Allo-Isoleucine in MSUD patients is a diagnostic marker of MSUD (Snyderman et al., *Pediatrics* 34:454-72, 1964).

The separation of Allo-Isoleucine from its enantiomer Isoleucine can be readily achieved by gas chromatography-mass spectrometry (GSMS). The mechanism of conversion from Isoleucine to Allo-Isoleucine is through an enol-keto tautomerization as confirmed by $N^{15}$-isotopic studies (Matthews et al., *Pediatr Res.* 14:854-7, 1980). In a normal individual, one of the intermediates in the pathway, i.e., (+)-keto-β-methyl-valeric acid, is a substrate for BCKDC, which prevents its accumulation, thereby thwarting the conversion of L-Isoleucine to L-Allo-Isoleucine (Matthews et al.). In MSUD positive patients, conversion from L-Isoleucine to L-Allo-Isoleucine takes place.

The methods described herein can be used to obtain specific and distinct measurements of Leu, Ile and allo-Ile.

Metabolic Profiling

The methods described herein can also be used to obtain a molecular profile for a sample and thus for a subject (e.g., a human, e.g., a newborn human). The profile can include information that indicates whether a particular molecular isomer of a branched-chain amino acid (e.g., leucine, isoleucine, allo-isoleucine and/or valine) is present and typically includes information about the presence (either qualitative or quantitative) of each isomer of a particular set.

Profiles can include the level of leucine, isoleucine, allo-isoleucine, and/or valine in a subject (e.g., a human patient, e.g., a newborn human patient). Other biomolecules can also be detected, quantitated, and/or evaluated, in a biological sample using tandem mass spectrometry. The resulting metabolic profile can be used for assessing the health of a subject (e.g., a human patient, e.g., a newborn human patient), such as presence or absence of a disorder, e.g., metabolic disorder, or for evaluating risk for a disorder.

A metabolic profile obtained by the methods described herein can be used in diagnosing or predicting susceptibility to a variety of metabolic disorders (e.g., MSUD) because the biochemical indicators (e.g., leucine, isoleucine, allo-isoleucine, and/or valine) examined can be indicative of such disorders, whether or not overt symptoms (e.g., physiologic or behavioral symptoms) of the disorder have become apparent.

A metabolic profile as described herein can be useful for monitoring the metabolism of a subject (e.g., a mammal such as a human), such as one undergoing treatment for a metabolic disorder. For example, the methods can be used for determining therapeutic efficacy of a particular treatment. Based on this determination, the subject can be offered additional or alternative therapeutic options. The metabolic profile can also be useful for assessing patient compliance with a particular treatment, such as a dietary restriction.

The methods described herein involve determining the presence or amount of at least one molecular isomer of a branched-chain amino acid, where the presence or amount of at least one amino acid correlates with the presence or absence of a metabolic disorder. The methods described herein can be used quantitatively, if desired, to allow comparison of test sample results with known or a pre-determined standard amount of a particular analyte(s) (e.g., by using an internal standard as described herein). In addition, or alternatively, the methods can be used qualitatively when a test sample is compared with a reference sample, which can be either a normal reference or metabolic disorder reference. In this format, the relative amount of amino acids can be indicative of a metabolic disorder. A reference sample, for example, can be from a subject that does not have the metabolic disorder in question.

Chemical Reaction Yields

The technology described herein can also be used in any application that requires separate measurement of Leu, Ile, or allo-Ile. For example, these techniques can be used to quantitate the yields of a synthetic reaction, e.g., to measure the concentration of one or more Leu, Ile, and allo-Ile.

By measuring a mixture of, e.g., Leu and Ile with a non-derivatized assay one can obtain the full complement of the combined concentrations (Leu+Ile). Measuring the mixture after derivatization, e.g., butylation, one obtains mainly the concentration of Leu in the mixture. Therefore, subtracting the concentration obtained with the derivatized assay from that obtained from the nonderivatized assay, the concentration of Ile can be obtained.

Methods of Identifying Compounds that Modulate Branched-Chain Amino Acid Levels

Also provided herein are methods of identifying compounds that modulate (e.g., decrease) the levels of molecular isomers of branched-chain amino acids, e.g., leucine, isoleucine, allo-isoleucine, and/or valine in vitro or in a cell or organism. Because disregulated levels of these amino acids are associated with increased risk of certain disorders (e.g., MSUD), compounds so identified could be useful in treating MSUD. Cells that can be contacted with the candidate compound can be of any species such that the cells produce leucine, isoleucine, allo-leucine, and/or valine (either synthetically or naturally). The cells can be primary cells or cell lines and can be of any histological type, e.g., without limitation, epithelial cells, fibroblasts, lymphoid cells, macrophages/monocytes, granulocytes, keratinocytes, neuronal cells, or muscle cells. The cells can be cultured in tissue culture dishes. Often it is preferable to grow the cells in multiwell assay plates (e.g., 96 well or 384 well assay plates) such that multiple candidate compounds can be evaluated at one time. The candidate compound (optionally at various concentrations ranging, e.g., from 0.001 nM to 10 mM) can be added to a solution (e.g., culture medium) containing the cells or, where the compound is a protein, the cells can recombinantly express it. Following incubation of cells expressing leucine, isoleucine, allo-leucine, and/or valine, the presence or level of leucine, isoleucine, allo-leucine, and/or valine can be determined using the mass spectrometry methods described herein. Prior to detection, the cells can be lysed and a sample is prepared from the lysate for tandem mass spectrometry. Often, a control compound can be added to a set of cells as either a positive or negative control, and evaluated in parallel.

The compounds identified in any of the methods described herein include various chemical classes. Compounds can be biomolecules including, but not limited to, proteins (e.g., enzymes), peptides, polypeptides, peptidomimetics (e.g., peptoids), amino acids, amino acid analogs, saccharides, fatty acids, steroids, purines, pyrimidines, derivatives or structural analogues thereof, polynucleotides, and polynucleotide analogs. Identification of test compounds through the use of the various libraries described herein permits subsequent modification of the test compound "hit" or "lead" to optimize the capacity of the "hit" or "lead" to modulate the levels of leucine, isoleucine, allo-leucine, and/or valine in a cell.

Mass Spectrometry

Tandem mass spectrometry can be used to distinguish and/or measure isomers. Typically, in tandem mass spectrometry, two mass analyzers are linked in series via a collision cell. The first mass analyzer (MS-1) is used to select an ion of interest (e.g., an ion of a particular mass-to-charge ratio (m/z)). The selected ions are then transferred to a collision cell where they are fragmented by collisions with an inert gas. Once the parent (sometimes referred to as precursor) ions have fragmented, the second mass analyzer (MS-2) is used to either scan and detect all of the produced daughter ions or to select and detect particular fragment ions. There are a number of mass analyzers available, e.g., quadrupoles, times-of-flight (TOF) analyzers, magnetic sectors, and both Fournier transform and quadrupole ion traps. Exemplary tandem mass spectrometers are available from: Waters Corporation, Thermoelectron, and Sciex. The most commonly used tandem mass spectrometers are electrospray triple quadrupoles.

Many mass spectrometers have mass accuracies to high resolution. For example, in the case of a singly charged ion, this range corresponds to 0.6 m/z. Minor variations (e.g., variations in the calibration) in a mass spectrometer may result in ion m/z signals that do not coincide with the ones stated herein, but the m/z signal corresponding to those disclosed can be easily identified and used, e.g., by compensating for offset in calibration.

Suitable samples for the methods described herein include any biological fluid, cell, tissue, or fraction thereof, that includes biomolecules, e.g., molecular isomers of branched-chain amino acids, indicative of a metabolic state. A sample can be, for example, a specimen obtained from a subject (e.g., a mammal such as a human) or can be derived from such a subject. For example, a sample can be a tissue section obtained by biopsy, or cells that are placed in or adapted to tissue culture. Exemplary samples therefore include cultured fibroblasts, cultured amniotic fluid cells, and chorionic villus sample. A sample can also be a biological fluid specimen such as urine, blood, plasma, serum, saliva, semen, sputum, cerebral spinal fluid, tears, mucus, and the like. A sample can be further fractionated, if desired, to a fraction containing particular cell types. For example, a blood sample can be fractionated into serum or into fractions containing particular types of blood cells such as red blood cells or white blood cells (leukocytes). If desired, a sample can be a combination of samples from a subject such as a combination of a tissue and fluid sample, and the like. Methods for obtaining samples that preserve the activity or integrity of molecules in the sample are well known to those skilled in the art. Such methods include the use of appropriate buffers and/or inhibitors, including nuclease, protease and phosphatase inhibitors, which preserve or minimize changes in the molecules in the sample. Such inhibitors include, for example, chelators such as ethylenediamne tetraacetic acid (EDTA), ethylene glycol bis(Paminoethyl ether)N,N,N1,N1-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Appropriate buffers and conditions for isolating molecules are well known to those skilled in the art and can be varied depending, for example, on the type of molecule in the sample to be characterized (see, for example, Ausubel et al. Current Protocols in Molecular Biology (Supplement 47), John Wiley & Sons, New York (1999); Harlow and Lane, Antibodies: A Laboratory Manual (Cold Spring Harbor Laboratory Press (1988); Harlow and Lane, Using Antibodies: A Laboratory Manual, Cold Spring Harbor Press (1999); Tietz Textbook of Clinical Chemistry, 3rd ed. Burtis and Ashwood, eds. W.B. Saunders, Philadelphia, (1999)).

A sample also can be processed to eliminate or minimize the presence of interfering substances. For use in the methods described herein, a sample can be in a variety of physical states. For example, a sample can be a liquid or solid, can be dissolved or suspended in a liquid, can be in an emulsion or gel, and can be absorbed onto a material. As a non-limiting example, a sample can be a liquid blood sample, liquid serum sample, liquid white blood cell sample, dried blood, serum, or white cell sample, or such a sample absorbed onto a paper or polymer substrate. Prior to performing mass spectrometry, a sample can be extracted using an extraction solution (see below). As further described below, the technology described herein requires some samples to be derivatized, e.g., esterified, e.g., to butyl-esters, prior to analysis using tandem mass spectrometry.

It is understood that modifications that do not substantially affect the activity of the various embodiments of this invention are also included within the definition of the invention provided herein. Accordingly, the following examples are intended to illustrate not to limit, the present invention.

EXAMPLES

Example 1

Discrimination Against One Isomer in a Leucine/Isoleucine Mixture

The following experiment demonstrates that there is a significant degree of differential butylation between leucine (Leu), and isoleucine (Ile).

Reference amino acid solutions containing Leu and Ile whose concentrations have been certified by the National Institutes of Standards and Technology were used to prepare solutions for analysis by MS/MS. A solution containing Leu and Ile at 2.31+/−0.09 and 2.24+/−0.07 µM concentrations, respectively, was processed according to the current practice by drying down the solution and exposing it to n-butanol in 3-N HCl to generate the corresponding butyl esters. The butyl esters from this solution were measured by tandem mass spectrometry. The experimental concentrations for the Leu/Ile mixture were determined with the aid of an internal standard ($^2H_3$Leu) already present in the solution at known concentration (4.55+/−0.19 µM).

If Leu and Ile were both completely butylated, the expected value for the concentration of the Leu/Ile mixture would be 4.55+/−35 µM This value would be determined by the abundance of the peak at m/z+188 with reference to the internal standard peak. The result obtained, however, was a concentration of 2.8+/−0.03 µM, indicating a significant difference between the expected and the experimental results. In fact, the result represented only 62% of the expected value, which is outside the expected experimental error.

The same solutions were tested by MS/MS using a method that does not require the butylation step. In this case, Leu and Ile appeared at m/z+132 and the internal standard at m/z+135. The results from this experiment indicated a concentration for the mixture of 4.1+/−0.05 µM, within the expected experimental error and representing 90% accuracy. This result demonstrated that the substantial deviation from expectation in the first experiment is attributed to the butylation reaction and led to the conclusion that butylation discriminates against one of the two amino acids in the mixture.

Example 2

Differential Esterification Efficiencies for Leucine, Isoleucine, and Allo-Isoleucine In order to elucidate which amino acid is discriminated during butylation, individual solutions of Leu, Ile, and allo-Ile were prepared each at 5 µM concentration. These solutions were analyzed by dispensing 100 µL of each solution in separate micro titer plate wells (six replicates of each) and dried down. Each of these wells then received 60 µL of a solution of n-butanol in 3 N HCl and the plate was incubated at 60° C. for 30 minutes. After incubation, the excess butanol and HCl were evaporated and the dried samples were reconstituted with 100 µL of a solution of acetonitrile and water (with 0.1% acetic acid) containing a 5 µM concentration of the internal standard $^2H_3$Leu. The samples were injected into a tandem mass spectrometer (ESI-Triple Quadrupole) and analyzed by a neutral loss scan of 46. This scan detects the amino acids that have not been esterified (i.e., non-reacted). Therefore, the use of this experiment in combination with the presence of the unesterified $^2H_3$Leu internal standard allowed the quantitation of the unesterified Leu, Ile, and allo-Ile independently.

The results of this experiment are presented in Table 1 below. As can be seen from this Table, there is significant evidence for differential butylation between these three amino acid isomers. In this experiment, the amount of unesterified amino acid was an indication of the degree of butylation. In the case of Leu, the presence of unesterified amino acid was 0.7 µM. This result indicated that Leu butylates very effectively and that approximately 86% of the Leu was butylated. In contrast, the amount of unesterified Ile determined in this experiment was 4.4 µM. This amount represents 88% of the original 5 µM Ile concentration. Therefore, only 12% of the initial Ile was butylated. Further, the quantitation of the unesterified allo-Ile in this experiment resulted in a concentration of 3.3 µM representing 66% of the original allo-Ile concentration. Thus only 34% of the original allo-Ile was butylated.

These results clearly indicate that there is significant differentiation in the butylation rates between these three amino acids and thus esterification can be used as a means for the differentiation of these three isomers by mass spectrometry.

TABLE 1

Butylation efficiencies of Leu, Ile and allo-Ile.

| Solution | non butylated portion µM | butylated portion µM (total - unbutylated) | butylation efficiency |
| --- | --- | --- | --- |
| $^2H_3$Leu and butylated Leu | 0.7 | 4.3 | 87% |
| $^2H_3$Leu and butylated Ile | 4.4 | 0.6 | 12% |
| $^2H_3$Leu and butylated allo-Ile | 3.3 | 1.7 | 34% |

Having determined that butylation does not occur at the same rate for all Leu isomers, the clinical impact of this differentiation was evaluated by measuring newborn dried blood spots with the derivatized assay. For this experiment, three identical sets of 288 samples each were processed as follows: set 1—derivatized assay; butylated Leu/Ile/allo-Ile were quantified; set 2—derivatized assay; internal standards were added during the reconstitution step; non-reacted Leu/Ile/allo-Ile were quantified; set 3—non-derivatized assay; non-derivatized Leu/Ile/allo-Ile were quantified. The results are shown in FIG. 3.

Figure 3:
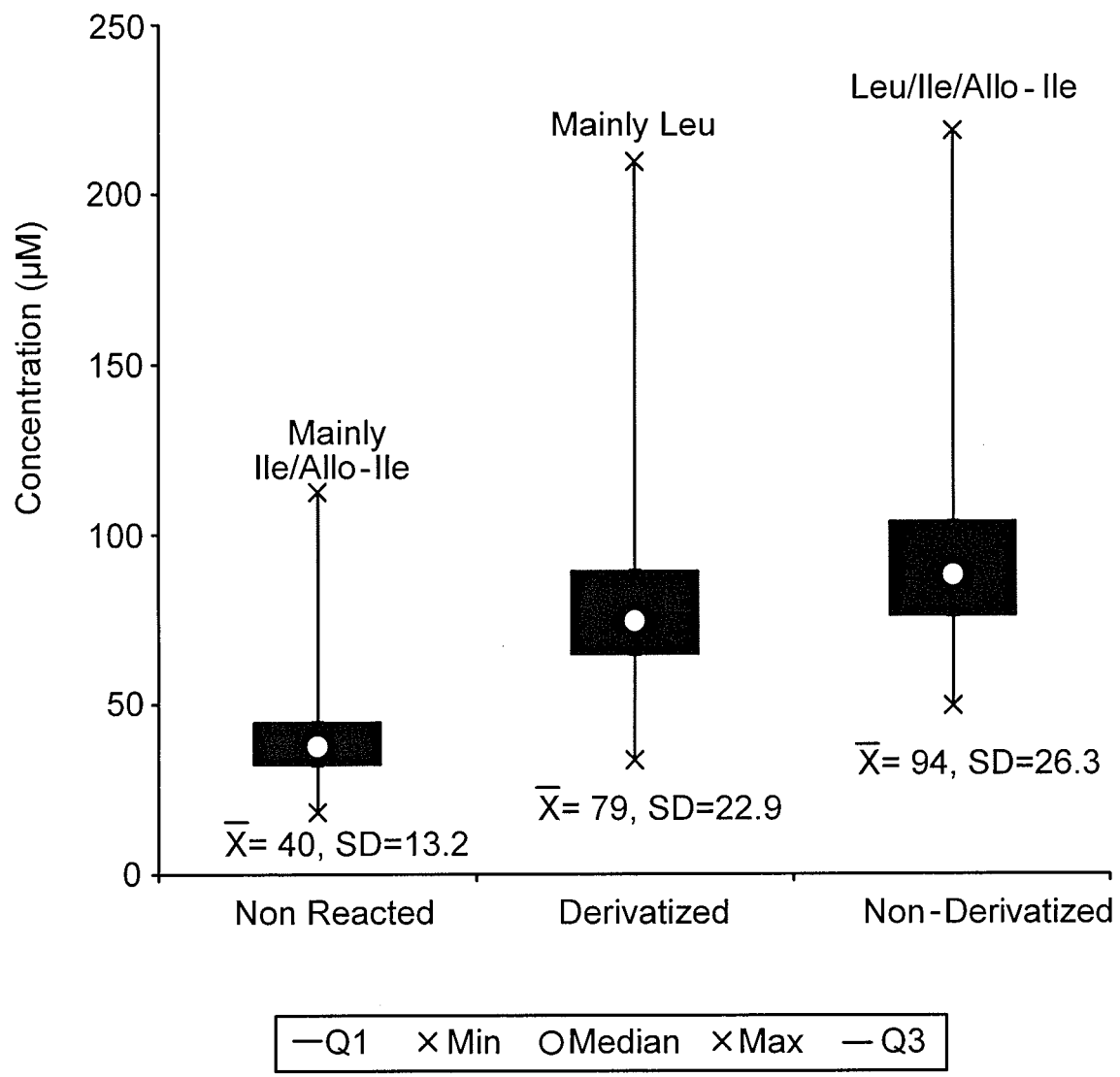
FIG. 3 is a graph depicting differential butylation in dried blood spots.

The box plots shown in FIG. 3 demonstrate that there was a significant difference between the derivatized and non-derivatized assays. The derivatized results were 84% of the non-derivatized values. Based on the butylation efficiencies, the difference can be accounted for by the non-reacted Ile/allo-Ile during the butylation step of the derivatized assay.

Overall, these results demonstrated that when using the derivatized assays, there is a high potential for discriminating against Ile and Allo-Ile. It is also noted that some samples, e.g., blood samples, usually contain a small amount of hydroxyproline, which is isobaric with the Leu isomers. The small amount of hydroxyproline, however, only contributes to the baseline of measurements.

These differential esterification efficiencies for Leu, Ile and allo-Ile have not been reported before. These differential efficiencies can be used to evaluate Leu, Ile and allo-Ile in a sample, e.g., in analytical applications that require the separate measurement of Leu from Ile, of Leu from allo-Ile, or of Ile from allo-Ile.

Example 3

Improved Separation of Leucine and Isoleucine

One implementation includes evaluating a sample from a newborn human. A dried blood spot sample can be obtained from a newborn. Dried blood spots from newborns are extracted with a methanolic solution and the extract is dried down. The sample can also include a standard with a non-derivatized amino acid, e.g., Leu. The dried extract and the internal standard are exposed to butanol in 3N HCl to generate n-butyl esters of the analytes of interest and of the standard. The excess n-butanol and HCl are evaporated and the derivatized sample is reconstituted in a solvent amenable for tandem mass spectrometry (MS/MS) analysis. The MS/MS analysis relies on the different mass-to-charge ratios (m/z) of analyte ions for their identification. In this approach, Val (m/z=+174, protonated molecular ion of Valine) is clearly distinguished from Leu, Ile and allo-Ile. However, Leu, Ile and allo-Ile are all structural isomers and thus all appear at the same m/z (+188) in the MS/MS experiment (see, e.g., FIG. 2). Therefore, when the blood sample from a newborn shows an elevated peak at m/z+188 it is assumed as a presumptive positive for MSUD, despite the fact that no indication is given by the assay regarding which of these three amino acids caused the elevation. Additionally, a biochemical MSUD indicative elevation of one of these three markers (e.g., Ile), might be artificially masked by high, but not disorder-indicative levels of another marker (e.g., Leu). Therefore, when MSUD screening results are based on the aggregate of Leu, Ile and allo-Ile appearing at +188 m/z transition, a false negative determination can be made.

After derivatization, e.g., butylation, an internal non-derivatized standard for Ile (e.g. $^2H_{10}$ Ile) is added. Additionally, data is acquired from the MS/MS scan known as neutral loss of 102 (the scan mode used to detect the amino acid butyl esters) and from a neutral loss scan of 46 (the scan mode used to detect the unbutylated amino acids) from the same sample.

Taking into consideration that upon butylation about 87% of Leu is transformed and that only about 12% of Ile and about 34% of allo-Ile are transformed, one expects to see in the non-derivatized scan about 13% of the original Leu in the sample plus about 88% of the original Ile and about 66% of the original allo-Ile in the sample. The non-derivatized Ile internal standard, provides a reference to quantitate the non-butylated species of these amino acids, while the derivatized Leu internal standard provides a reference to quantitate the butylated species. This method, therefore, effectively separates Ile/allo-Ile from Leu and thus provides a more accurate measurement.

Because Leu is the analyte of highest contribution to the endogenous levels, the ability to reduce its contribution to the signal increases sensitivity for detecting changes in Ile/allo-Ile concentration. Changes in Ile and allo-Ile concentrations are thus more noticeable by measuring the non-butylated species. At the same time, the butylated species are generally free of Ile/allo-Ile and therefore provide a more accurate measurement of Leu and its changes.

Figure 4A:
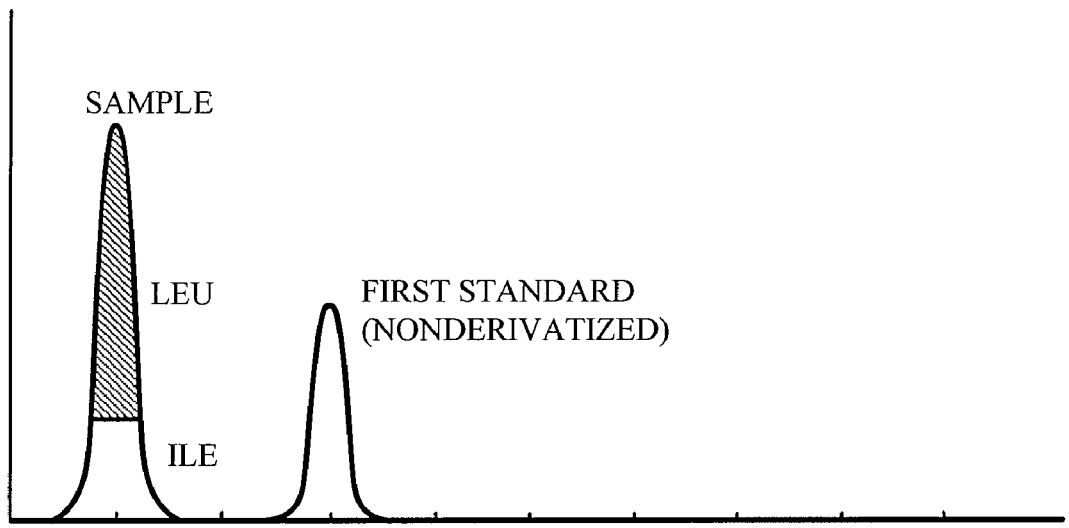
FIG. 4A is a schematic of two types of mass spectral peaks that can be obtained from leucine and isoleucine sample and from a first nonderivatized standard.
Figure 4B:
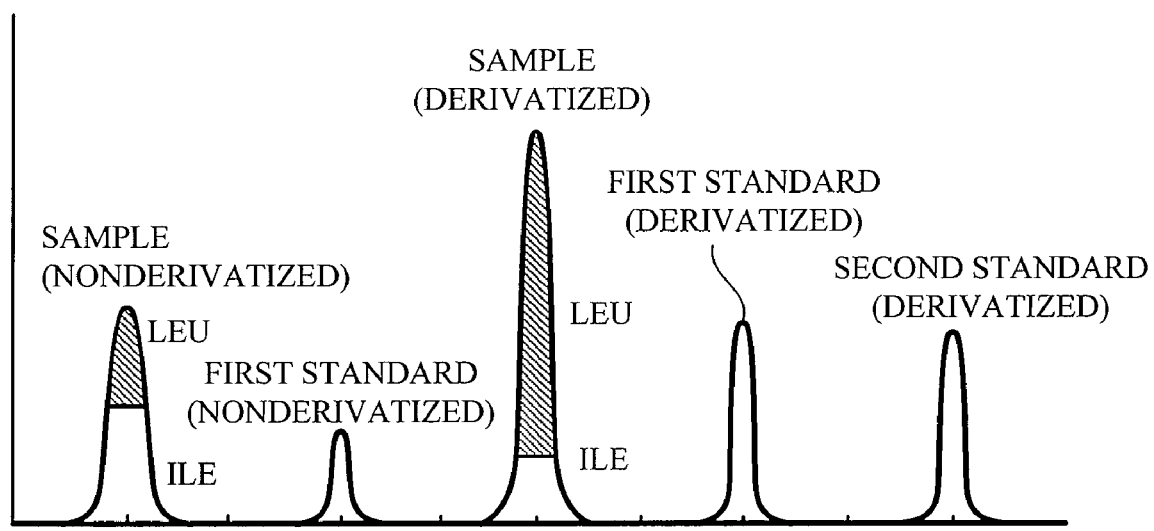
FIG. 4B is a schematic of five types of mass spectral peaks that can be obtained after processing the samples from FIG. 4A.

These techniques can utilize various combinations of internal standards to quantify the derivatized and nonderivatized isoforms. Referring now to the example in FIG. 4A, a first nonderivatized internal standard of Leu, Ile, or allo-Ile is added to the sample to be analyzed. A schematic of the mass spectra of the sample and the first standard is shown in FIG. 4A. In some implementations, two or more nonderivatized standards are added, e.g., a standard of Leu, a standard of Ile, and/or a standard of allo-Ile (each labeled with a different heavy atom isotope). After processing, a second derivatized internal standard (including leucine, isoleucine or allo-isoleucine) is added. A schematic of mass spectra that are obtained after addition of the second standard is shown in FIG. 4B. (FIGS. 4A and 4B (as well as 5A and 5B below) are schematics, and were not based on an actual implementation). Known concentrations of the first and second standards are used to quantitate the concentrations of derivatized and non-derivatized forms of the first standard after processing to obtain derivatization efficiency. Derivatization efficiency is then used to obtain concentrations of derivatized and non-derivatized leucine and isoleucine in the processed samples.

Figure 5A:
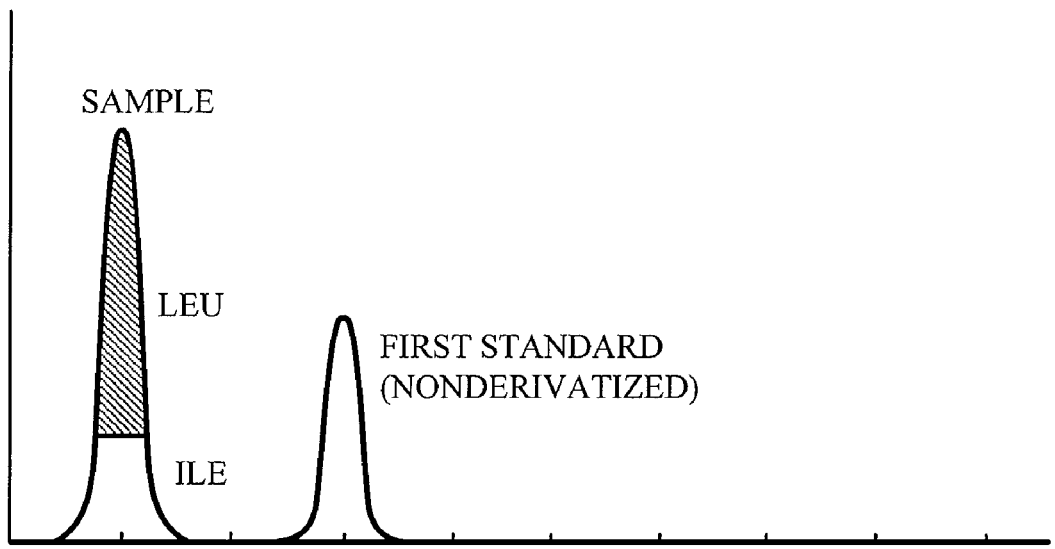
FIG. 5A is a schematic of two types of mass spectral peaks that can be obtained from leucine and isoleucine sample and from a first nonderivatized standard.
Figure 5B:
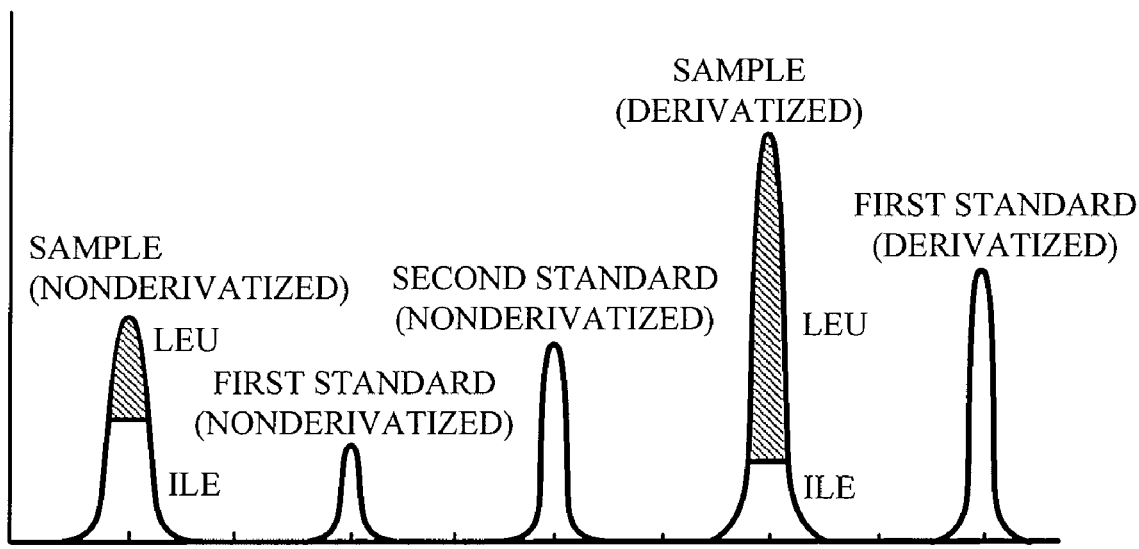
FIG. 5B is a schematic of five types of mass spectral peaks that can be obtained after processing the samples from FIG. 5A.

In another implementation, a first nonderivatized internal standard of Leu, Ile, or allo-Ile is added to the sample to be analyzed. A schematic of the mass spectra of the sample and the first standard is shown in FIG. 5A. In some implementations, two or more nonderivatized standards are added, e.g., a standard of Leu, a standard of Ile, and/or a standard of allo-Ile (each labeled with a different heavy atom isotope). After processing, a second non-derivatized internal standard (including Leu, Ile, or allo-Ile) is added. A schematic of mass spectra that can be obtained after addition of the second standard is shown in FIG. 5B. Known concentrations of the first and second standards are used to quantitate the concentrations of derivatized and nonderivatized forms of the first standard after processing and obtain derivatization efficiency. Derivatization efficiency is then used to quantitate the concentrations of derivatized and non-derivatized leucine and isoleucine in the samples.

The methods described herein can include the use of not only one, but at least two, e.g., two to five internal standards. It is possible to use one, two or three nonderivatized standards (each including one of Leu, Ile, and/or allo-Ile) that are added prior to derivatization of a sample, a derivatized internal standard that is added after derivatization (including Leu, Ile, or allo-Ile), and/or a non-derivatized internal standard that is added after derivatization (including Leu, Ile, or allo-Ile). Generally, each standard is added at a known concentration and each is labeled with a different heavy atom isotope. If multiple standards are used, they can be distinguished from one another by the incorporation of different isotopic labeling, so that their resulting masses are distinguishable.

These techniques can be further optimized, e.g., by changing the temperature of incubation during the esterification step or changing the incubation time. Conditions can be selected to further impair esterification of one isomer relative to another, e.g., to impair esterification of Ile and thus obtain an even more specific measurement of Leu. Additionally, changing the concentration of acid in the esterification reagent can be used to increase the resolution between these isomeric species.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. A method of detecting a presence or absence of leucine or an isomer thereof in a sample, the method comprising:
    providing a test sample;
    adding to the test sample a first standard comprising a first amino acid that is labeled with one or more heavy atoms, thereby providing a modified test sample, wherein the first amino acid is leucine or an isomer thereof;
    subjecting the modified test sample to esterification conditions, thereby providing an esterified sample;
    adding to the esterified sample a second standard comprising an esterified form or a non-esterified form of a second amino acid that is labeled with one or more heavy atoms, thereby providing a modified esterified sample, wherein the second amino acid is leucine or an isomer thereof;
    evaluating the modified esterified sample using tandem mass spectrometry; and
    detecting signals indicative of esterified and non-esterified forms of at least two different amino acids in the modified esterified sample, wherein the at least two different amino acids are selected from leucine and isomers of leucine, thereby distinguishing between the at least two amino acids and detecting the presence or absence of leucine or an isomer thereof in the test sample.

2. The method of claim 1, wherein the esterification conditions provide an esterified form of the first standard, wherein the second standard comprises the esterified form of the second amino acid, and wherein the esterified form of the first standard and the second standard have different molecular weights as a result of different heavy atom labeling.

3. The method of claim 1, wherein the second standard comprises the non-esterified form of the second amino acid, and wherein the first standard prior to the esterification conditions and the second standard have different molecular weights as a result of different heavy atom labeling.

4. The method of claim 1, further comprising determining an esterification efficiency of leucine or an isomer thereof by reference to the first standard and the second standard.

5. The method of claim 4, further comprising determining a concentration of leucine or an isomer thereof in the test sample using the esterification efficiency.

6. The method of claim 1, wherein the at least two different amino acids include one at least two of leucine, isoleucine, and allo-isoleucine.

7. The method of claim 1, wherein the esterification conditions are carried out with an alcohol.

8. The method of claim 7, wherein the alcohol is selected from the group consisting of butanol, isopropyl alcohol, ethanol, and methanol.

9. The method of claim 1, wherein during the esterification conditions, less than 100% of the first amino acid is esterified.

10. The method of claim 1, wherein the first standard is selected from the group consisting of labeled leucine, labeled isoleucine, and labeled allo-isoleucine.

11. The method of claim 1, wherein the second standard is selected from the group consisting of labeled leucine, labeled isoleucine, and labeled allo-isoleucine.

12. The method of claim 1, wherein the detecting signals comprises acquiring data signals representing butylated and unbutylated forms of leucine or an isomer thereof.

13. A method of diagnosing a metabolic disorder, the method comprising:
    providing a test sample from a subject;
    adding to the test sample a first standard comprising a first amino acid that is labeled with one or more heavy atoms, thereby providing a modified test sample, wherein the first amino acid is leucine or an isomer thereof;
    subjecting the modified test sample to esterification conditions, thereby providing an esterified sample;
    adding to the esterified sample a second standard comprising an esterified form or a non-esterified form of a second amino acid that is labeled with one or more heavy atoms, thereby providing a modified esterified sample, wherein the second amino acid is leucine or an isomer thereof;
    evaluating the modified esterified sample using tandem mass spectrometry; and
    detecting signals indicative of esterified and non-esterified forms of at least two different amino acids in the modified esterified sample, wherein the at least two different amino acids are selected from leucine and isomers of leucine, thereby distinguishing between the at least two amino acids and determining a level of leucine or an isomer thereof in the test sample;
    wherein the level of the leucine or the isomer thereof in the test sample being altered relative to a level of leucine or isomer thereof in one or more reference samples is an indication that the subject has, or is at risk of developing, a metabolic disorder characterized by an altered level of the leucine or the isomer thereof.

14. The method of claim 13, wherein the metabolic disorder is Maple Syrup Urine Disorder (MSUD).

15. The method of claim 13, wherein the subject is a human.

16. The method of claim 13, wherein the subject is a newborn human.

17. The method of claim 13, further comprising determining an esterification efficiency of leucine or an isomer thereof by reference to the first standard and the second standard.

18. The method of claim 17, further comprising determining a concentration of leucine or an isomer thereof in the test sample using the esterification efficiency.

19. The method of claim 13, wherein the at least two different amino acids include at least two of leucine, isoleucine, and allo-isoleucine.

20. The method of claim 13, wherein the esterification conditions provide an esterified form of the first standard, wherein the second standard comprises the esterified form of the second amino acid, and wherein the esterified form of the first standard and the second standard have different molecular weights as a result of different heavy atom labeling.

21. The method of claim 13, wherein the second standard comprises the non-esterified form of the second amino acid, and wherein the first standard prior to the esterification conditions and the second standard have different molecular weights as a result of different heavy atom labeling.

22. The method of claim 13, wherein the esterification conditions are carried out with an alcohol.

23. The method of claim 22, wherein the alcohol is selected from the group consisting of butanol, isopropyl alcohol, ethanol, and methanol.

24. The method of claim 13, wherein during the esterification conditions, less than 100% of the first amino acid is esterified.

25. The method of claim 13, wherein the first standard is selected from the group consisting of labeled leucine, labeled isoleucine, and labeled allo-isoleucine.

26. The method of claim 13, wherein the second standard is selected from the group consisting of labeled leucine, labeled isoleucine, and labeled allo-isoleucine.

* * * * *

UNITED STATES PATENT AND TRADEMARK OFFICE
CERTIFICATE OF CORRECTION

PATENT NO. : 8,247,236 B2
APPLICATION NO. : 13/084250
DATED : August 21, 2012
INVENTOR(S) : Blas Cerda, Alex Cherkasskiy and Yijun Li It is certified that error appears in the above-identified patent and that said Letters Patent is hereby corrected as shown below:

Page 1, column 2 (other publications), line 6:
delete "eserification" and replace with -- esterification --.

Page 1, column 2 (other publications), line 7:
delete "n-propano," and replace with -- n-propanol, --.

Column 15, line 44:
in claim 6, after "include" delete "one".

Signed and Sealed this
Twentieth Day of November, 2012

David J. Kappos
*Director of the United States Patent and Trademark Office*